United States Patent [19]

Taniguchi et al.

[11] Patent Number: 5,252,371
[45] Date of Patent: Oct. 12, 1993

[54] REWRITABLE PHOTOCHROMIC OPTICAL DISK

[75] Inventors: Hitoshi Taniguchi; Fumio Matsui, both of Tsurugashima; Tsuneki Okazaki; Masaaki Hayami, both of Okayama, all of Japan

[73] Assignee: Pioneer Electronic Corporation, Tokyo, Japan

[21] Appl. No.: 892,128

[22] Filed: Jun. 2, 1992

[30] Foreign Application Priority Data

Sep. 13, 1991 [JP] Japan .................... 3-235144

[51] Int. Cl.$^5$ .............................................. B32B 3/00
[52] U.S. Cl. ............................ 428/64; 428/65; 428/457; 428/913; 430/945; 346/76 L 135.1; 369/288
[58] Field of Search ............... 428/64, 65, 457, 913; 430/945; 346/76 L, 135.1; 369/288

[56] References Cited

U.S. PATENT DOCUMENTS

| | | | |
|---|---|---|---|
| 4,837,063 | 6/1989 | Irie | 428/64 |
| 5,061,582 | 10/1991 | Brettle et al. | 430/19 |

Primary Examiner—Patrick J. Ryan
Assistant Examiner—Elizabeth Evans
Attorney, Agent, or Firm—Keck, Mahin & Cate

[57] ABSTRACT

A rewritable photochromic optical disk comprises a photochromic recording layer made of a dibenzothienyl ethene derivative, 1,2-di(2-cyano-3-benzothienyl)-1,2-dicyanoethene capable of assuming first and second states, the first state with a first absorption band transforming into the second state with a second absorption band by irradiating a first light beam of a first wavelength, and the second state transforming into the first state by irradiating a second light beam of a second wavelength in the second absorption band. This rewritable photochromic optical disk has a stability in the repeated recording and erasing information and a high thermal stability and capable of storage of information extended over a long period of time, in accordance with its higher quantum yield than that of the conventional dibenzothienyl ethene derivative so that the achromatic reaction takes place by irradiation of a low power laser beam.

4 Claims, 1 Drawing Sheet

REWRITABLE PHOTOCHROMIC OPTICAL DISK

BACKGROUND OF THE INVENTION

1. Field of the Invention

The present invention relates to a rewritable photochromic optical disk having a photochromic recording layer.

2. Description of the Related Art

The photochromic optical disk making use of the isomerization reaction with light and heat which is reversible as in the organic photochromic materials, is known as one of the rewritable memories capable of recording, reading, and erasing such as an Erasable Direct Read After Writing (EDRAW) optical disk.

Such an erasable optical disk is produced by the following process. As shown in FIG. 1, a recording layer 2 including the organic photochromic material is formed as a thin film on a transparent substrate 1 and then an aluminum-made reflecting layer 3 is formed on the recording layer 2 in the form of a thin-film. A protective layer 4 is formed on the reflecting layer 3. On the main surface of the substrate 1, grooves used for tracking, prepits for controlling the writing and reading of data, and pre-addresses 5 are formed in advance by the process of stamping or the like. A laser beam 6 is irradiated on the the recording layer 2 of photochromic material through the substrate 1 of the disk.

The organic photochromic materials are compounds which react with light to repeatedly change from a chromatic state to an achromatic state or vice versa. As shown in light-absorption spectral distribution curves of FIG. 2 by way of example, the materials have the following characteristics. When light of a predetermined wavelength B is absorbed by the organic photochromic material, the material changes from a stable state X (first state) to a quasi-stable state Y (second state) in which it is rendered chromatic (chromatic reaction). When it absorbs light of another predetermined wavelength A or heat under the quasi-stable state, it returns to the original material again and is render achromatic (achromatic reaction). By utilizing the above described phenomenon i.e., photochromism, a rewritable optical disk is manufactured, to and from which information is recorded, reproduced, or erased by a laser beam. As such organic photochromic materials, there are for example, those materials such as thioindigo which make use of the isomerization reaction with light, spiropiranes which utilize the ring opening/closure reaction and a redox reaction or the like, and flugido, etc. In addition, other organic photochromic materials of diaryl ethene derivatives are disclosed in U.S. Pat. No. 4,837,063.

Recording of information on the optical disk is performed by applying energy of light and/or heat to the recording layer 2 by means of a writing laser beam in the form of spots through an optical pickup system to generate the chromatic reactions positively in the spots, thereby forming a train of chromatic spots in turn. The reading of information from the optical disk is performed by irradiating a reading laser beam having another wavelength so as to read out the train of the spots which have been recorded. The erasing of information from the optical disk is performed by irradiating a erasing laser beam having another wavelength to the train of the spots which have been recorded.

On the other hand, there is desired a rewritable photochromic optical disks capable of being recorded an played back information therefrom even by using a low power laser beam during the repeated writing, reading and erasing operations. However such optical disks do not been developed yet.

SUMMARY OF THE INVENTION

It is therefore an object of the present invention to provide a rewritable photochromic optical disk capable of being recorded and played back information therefrom even by repeatedly irradiating a low power laser beam thereto for the purpose of storage of information extended over a long period of time.

The rewritable photochromic optical disk according to the present invention comprises a photochromic recording layer made of a dibenzothienyl ethene derivative capable of assuming first and second states, the first state with a first absorption band transforming into the second state with a second absorption band by irradiating a first light beam of a first wavelength, and the second state transforming into the first state by irradiating a second light beam of a second wavelength in said second absorption band, wherein the dibenzothienyl ethene derivative in the first state is represented by the following formula 1

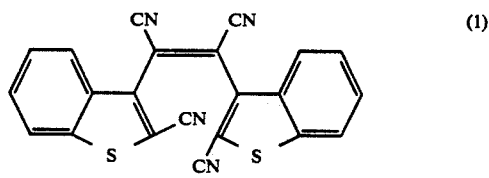

and the dibenzothienyl ethene derivative in the second state is represented by the following formula 2.

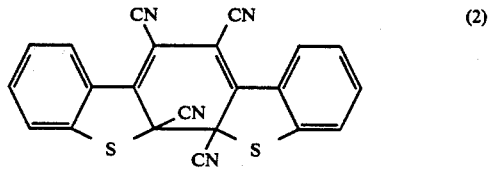

The rewritable photochromic optical disk constructed as mentioned above obtains a stability in the repeated recording and erasing information and a high thermal stability since the quantum yield of said dibenzothienyl ethene derivative is higher than that of the conventional dibenzothienyl ethene derivative so that the achromatic reaction takes place by irradiation of a low power laser beam.

DESCRIPTION OF THE PREFERRED EMBODIMENT

The embodiment of the present invention will be described with reference to the accompanying drawings.

Figure 1:
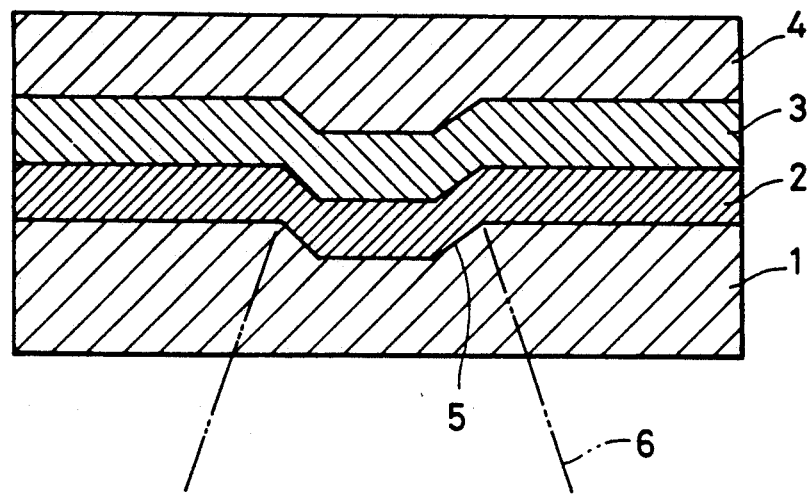
FIG. 1 is a partly enlarged sectional view of the rewritable photochromic optical disk.
Figure 2:
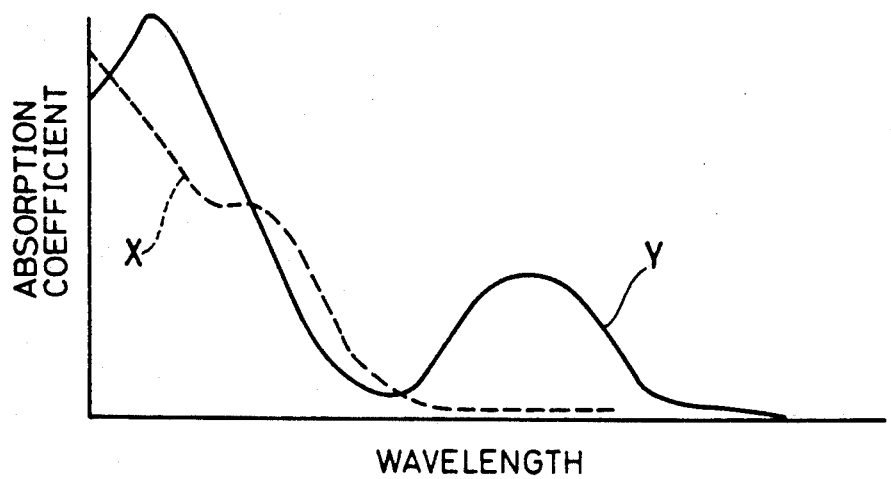
FIG. 2 is a graph showing the distribution of light absorptance spectrum of an organic photochromic material.

The rewritable photochromic optical disk of the present invention is similar to the conventional one shown in FIG. 1, except the recording layer. It is made up of a substrate 1 and three layers/photochromic layer 2, reflective layer 3, and protective layer 4 consecutively formed thereon.

According to the present invention, the photochromic layer in the rewritable photochromic optical disk is made of a dibenzothienyl ethene derivative, 1,2-di(2-cyano-3-benzothienyl)-1,2-dicyanoethene. This compound has the structure as represented by formula 1 below when assumes the first state achomatic.

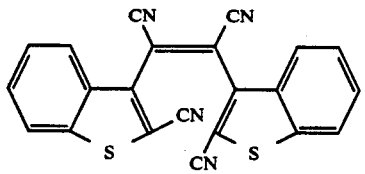
(1)

When this photochromic recording layer is irradiated a with a ray of light having a wavelength of 420 nm (a first wavelength) and an adequate intensity, the derivative assumes the second state chomatic, thereby forming a closed ring as represented by formula 2 below.

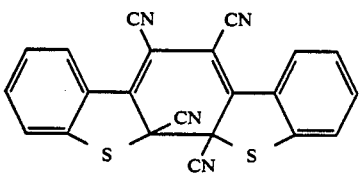
(2)

Next, when the photochromic recording layer in the second state is exposed to a ray of light having a wavelength 500 nm (the second wavelength) in the second absorption band and an adequate intensity, the derivative assumes the first state achomatic forming a open ring again as represented by formula 1.

The rewritable photochromic optical disk in the above-mentioned embodiment permits the recording of the logical values "0" and "1", because the recording layer assumes two states. The first state may be regarded as an initial state representing the logical value "0". Then, the first state is transformed into the second state for writing the value "1" by the irradiation of a laser beam having a first wavelength of 400 nm. The second state can be returned to the first state for erasing "1" by the irradiation of a laser beam having a second wavelength of 500 nm. The recording of tertiary logical states permits on this rewritable photochromic optical disk.

Inventors revealed that the substance represented by formulas 1 and 2 of this rewritable photochromic optical disk had a high quantum yield as a result from an investigation of quantum yields in various dibenzothienyl ethene derivatives.

The benzene solution of 0.1 m moles was prepared at 25° C., which contained the dibenzothienyl ethene derivative of formula 1. As comparatives, benzene solutions at the same conditions containing dithienyl ethene and dibenzothienyl ethene derivatives represented by formulas 3 and 5 below were prepared respectively.

The first comparative dithienyl ethene derivative, 1,2-di(2,4,5-trimethyl-3-thienyl)-1,2-dicyanoethene has the structure as represented by formula 3 below when assumes the first state achomatic.

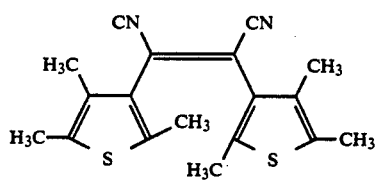
(3)

When this photochromic material in the first state is irradiated with a ray of light having a wavelength of 420 nm, it assumes the second state chomatic represented by formula 4 below.

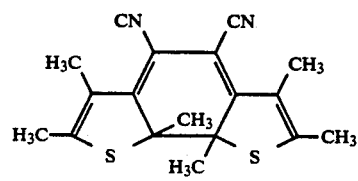
(4)

When this photochromic material in the second state is exposed to a ray of light having a wavelength 520 nm, it assumes the first state achomatic again as represented by formula 3.

The second comparative dibenzothienyl ethene derivative, 1,2-di(2-methyl-3-benzothienyl)-1,2-dicyanoethene has the structure as represented by formula 5 below when assumes the first state achomatic.

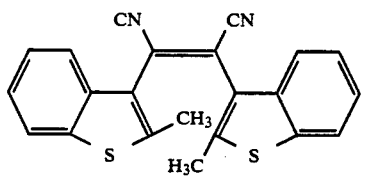
(5)

When this photochromic material in the first state is irradiated with a ray of light having a wavelength of 420 nm, it assumes the second state chomatic represented by formula 6 below.

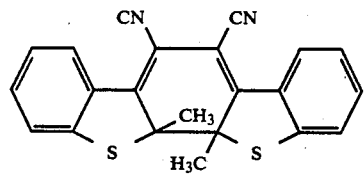
(6)

When this photochromic material in the second state is exposed to a ray of light having a wavelength 510 nm, it assumes the first state achomatic again as represented by formula 5.

These photochromic material solutions were exposed to light of wavelength 420 nm and in chromatic states of absorption coefficient 0.3 respectively. After that the quantum yields of the materials were measured in their opened reactions by irradiations of light beams having peak wavelengths 500 nm, 520 nm and 510 nm respectively.

The resulting quantum yields of the dibenzothienyl ethene derivative in the present invention and the first and second comparative materials were as follows:

The quantum yield of the present derivative in the achromatic reaction represented by formulas 2 to 1:0.9

The quantum yield of the first comparative derivative in the achromatic reaction represented by formulas 4 to 3:0.15

The quantum yield of the second comparative derivative in the achromatic reaction represented by formulas 6 to 5:0.4

These results shows that the quantum yield of the present dibenzothienyl ethene derivative is higher than those of the conventional dithienyl ethene and dibenzothienyl ethene derivatives in the achromatic reactions.

As mentioned above, the rewritable photochromic optical disk according to the present invention comprises a photochromic recording layer made of a dibenzothienyl ethene derivative capable of assuming first and second states, the first state with a first absorption band transforming into the second state with a second absorption band by irradiating a first light beam of a first wavelength, and the second state transforming into the first state by irradiating a second light beam of a second wavelength in said second absorption band, wherein the dibenzothienyl ethene derivative in the first state is represented by above formula 1 and in the second state is represented by above formula 2. Such a rewritable photochromic optical disk has a stability in the repeated recording and erasing information and a high thermal stability in accordance with its higher quantum yield than that of the conventional dibenzothienyl ethene derivative so that the achromatic reaction takes place by irradiation of a low power laser beam. Such a rewritable photochromic optical disk is therefore capable of storage of information extended over a long period of time.

What is claimed is:

1. A rewritable photochromic optical disk comprising a photochromic recording layer made of a 1,2-di(2-cyano-3-benzothienyl)-1,2-dicyanoethene capable of assuming first and second states, the first state with a first absorption band transforming into the second state with a second absorption band by irradiating a first light beam of a first wavelength, and the second state transforming into the first state by irradiating a second light beam of a second wavelength in said second absorption band, wherein the dibenzothienyl ethene derivative int he first state is represented by the following formula 1

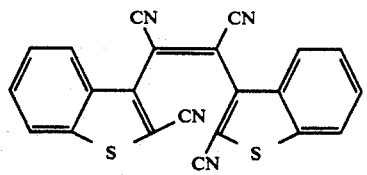
(1)

and the dibenzothienyl ethene derivative in the second state is represented by the following formula 2.

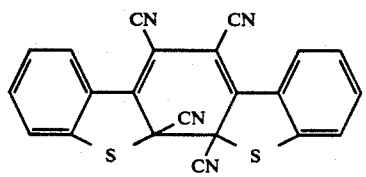
(2)

2. A rewritable photochromic optical disk comprising a photochromic recording layer made of a 1,2-di(2-cyano-3-benzothienyl)-1,2-dicyanoethene capable of assuming first and second states, the first state with a first absorption band transforming into the second state with a second absorption band by irradiating a first light beam of a first wavelength, and the second state transforming into the first state by irradiating a second light beam of a second wavelength in said second absorption band, wherein the dibenzothienyl ethene derivative in the first state is represented by the following formula 1

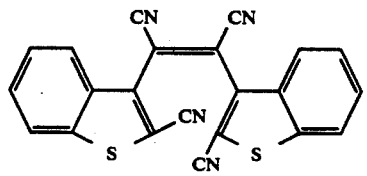
(1)

and the dibenzothienyl ethene derivative in the second state is represented by the following formula 2

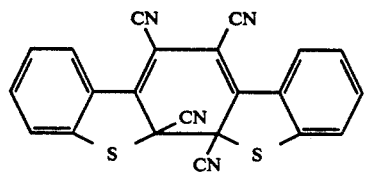
(2)

wherein said photochromic recording layer is formed on a transparent substrate.

3. A rewritable photochromic optical disk as claimed in claim 2, wherein said photochromic recording layer is covered with a reflective layer.

4. A rewritable photochromic optical disk comprising a photochromic recording layer made of a 1,2-di(2-cyano-3-benzothienyl)-1,2-dicyanoethene capable of assuming first and second states, the first state with a first absorption band transforming into the second state with a second absorption band by irradiating a first light beam of a first wavelength, and the second state transforming into the first state by irradiating a second light beam of a second wavelength in said second absorption band, wherein the dibenzothienyl ethene derivative in the first state is represented by the following formula 1

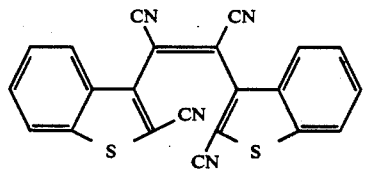
(1)

and the dibenzothienyl ethene derivative in the second state is represented by the following formula 2

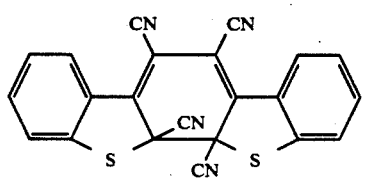
(2)

wherein said photochromic recording layer is covered with a reflective layer.

* * * * *